(12) United States Patent
Tai et al.

(10) Patent No.: US 8,658,806 B2
(45) Date of Patent: Feb. 25, 2014

(54) PROCESS FOR PREPARING OPTICALLY ACTIVE ANTROCIN

(75) Inventors: Dar-Fu Tai, Hualien (TW); Venkatachalam Angamuthu, Hualien (TW); Yew-Min Tzeng, Taichung (TW)

(73) Assignee: Deyew Biotech Corp., Taichung (TW)

( * ) Notice: Subject to any disclaimer, the term of this patent is extended or adjusted under 35 U.S.C. 154(b) by 0 days.

(21) Appl. No.: 13/618,016

(22) Filed: Sep. 14, 2012

(65) Prior Publication Data

US 2013/0096324 A1   Apr. 18, 2013

(30) Foreign Application Priority Data

Oct. 17, 2011   (TW) .............................. 100137549 A (51) Int. Cl.
*C07D 407/00* (2006.01)
(52) U.S. Cl.
USPC ........................................................ 549/300
(58) Field of Classification Search
USPC ........................................................ 549/300
See application file for complete search history.

(56) References Cited

PUBLICATIONS

Dailey et al. Journal of Organic Chemistry (1980), 45(2), 216-36.*
Utimoto et al. Tetrahedron (1983), 39(6), 967-73.*
Sanz-Burata et al. Afinidad (1970), 27(281), 705-14.*

* cited by examiner

*Primary Examiner* — Nizal Chandrakumar
(74) *Attorney, Agent, or Firm* — WPAT, P.C.; Anthony King (57) ABSTRACT

The present invention relates to a process of preparation of optically active antrocin. At first, to introduce the correct configuration of trans-decalone, alkyl aluminum/TMSCN was used to react with decalenone. The resulting racemic nitrile-decalone was resolved with chiral diol by ketalization to produce two chromatography separable diasteromers. After a simple column chromatography, optically pure compounds were obtained. Formylation was a critical step for the lactone formation. The rest of the synthesis is straight forward through oxidation and olefination. Accordingly, the total synthesis was completed in 10 steps with 7% overall yield from commercially available 6-methoxy-2-tetralone.

11 Claims, 10 Drawing Sheets

PROCESS FOR PREPARING OPTICALLY ACTIVE ANTROCIN

FIELD OF THE INVENTION

The present invention relates to a method of organic synthesis with a technique of optical resolution. The diastereomers formed by natural dimethyl tartarate can be successfully isolated by silica gel column. The obtained ketal optical isomer can be applied to synthesis of antrocin.

BACKGROUND OF THE INVENTION

*Antrodia camphorata*, a medicinal fungus, is used as tonic in Taiwan folk medicine with antidotes function. It plays an important role in treatment of alcohol and drug intoxication and itchy skin and also has anti-tumor efficacy. Antrocin is isolated from methanol extract of *Antrodia camphorata* and characterized by X-ray diffraction for the three-dimensional structure of sesquiterpene lactones compound (Chiang, H. C., Wu, D. P., Cherng, I. W., Ueng, C. H. *Phytochem.* 1995, 39, 613-616). Recently, antrocin is proved to be a potent antagonist of a variety of cancers, against MDA-MB-231 cells of metastatic breast cancer with an $IC_{50}$ value of 0.6 μM, as well as dual inhibitor of Akt/mTOR (Rao, Y. K., Wu, A. T. H., Geethangili, M., Huang, M. T., Chao, W. J., Wu, C. H., Deng, W. P., Yeh, C. T., Tzeng, Y. M. Chem. Res. Toxicol. 2011, 24, 238-245). Thus, it arouses high interest. Among the identified compounds isolated and purified from *Antrodia camphorate*, antrocin with small molecular weight (MW=234) has special bioactivity and potential to be developed into clinical trials reagents for treating metastatic breast cancer. The needs for antrocin in biomedical community are of considerable importance, but there are many issues to be resolve due to current technique. In terms of quantity and method, antrocin obtained from nature have certain limitations. Only synthetic method is sufficient to meet the vast needs of the market. There are no literature reports the same process to synthesize racemic antrocin, and no one uses the same synthetic process to synthesize optically active antrocin.

Figure 1:
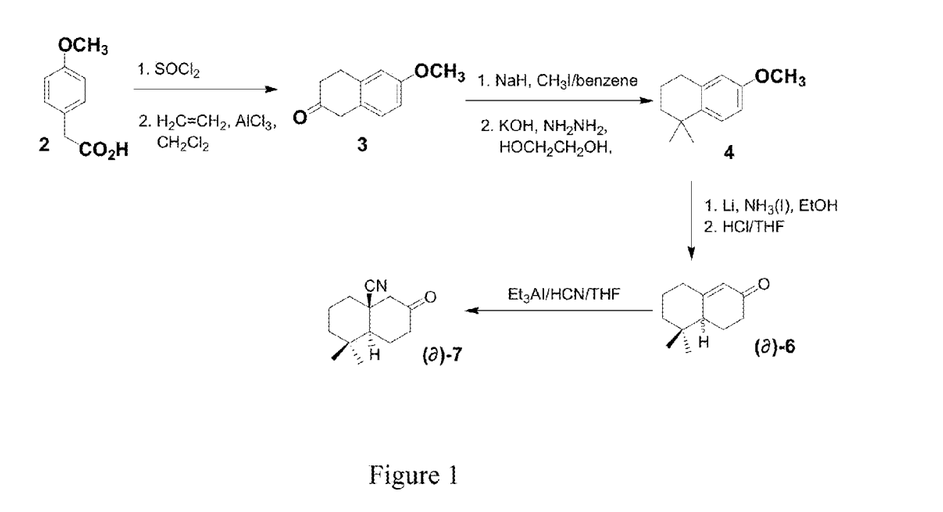
FIG. 1 shows the pathway of Fuchs synthesis of 1,1-dimethyl-6-oxo-decahydronaphthalene-4a-carbonitrile.

In previous synthetic technique, there have been related literature reported (Dailey, O. D. Jr., Fuchs, P. L., J. Org. Chem. 1980, 45, 216-236; Armour, A. G., Buchi, G., Eschenmoser, A., Storni, A., *Helv. Chim. Acta.,* 1959, 42, 2233.), as shown in FIG. 1. The trans-compound (±)-7 could be prepared appropriately through pathway of racemic compound (±)-6 formed from 4-methoxy-phenylaceitic acid and cyanide addition reaction.

Although using such synthesis techniques can roughly synthesize the needed racemic structure of trans-decalone, the follow-up process requires tedious modification and some special and expensive reagents to have a chance to achieve the synthesis of racemic antrocin. However, under these stringent conditions, the synthesis still generates more racemic byproduct remained. It will increase the process of separation and purification, and also has great risk behind, comprising some possible toxic substances in the end product. Therefore, the greatest challenge lies in chiral synthesis of optical isomers. It is necessary to perform optical resolution first, resulting in an optically active intermediate, thereby synthesizing antrocin compound in a straightforward manner to perform the process, in order to reduce the price of the product and enhance its purity and practicality.

SUMMARY OF THE INVENTION

The present invention provides a method for preparing an optically active antrocin of formula I, comprising:

reacting compound of formula V

V with a methylenation reagent to obtain the compound of formula I.

DETAILED DESCRIPTION OF THE INVENTION

The present invention provides a method for preparing optically active antrocin of formula I, comprising:

I reacting a compound of formula V

V with a methylenation reagent to obtain compound of formula I. Preferably, the methylenation reagent is Lombardo reagent, dimethylzinc, or a mixture of zinc powder, 1,2-dibromoethane, dibromomethane, and trimethylsilyl chloride.

The compound of formula V is formed by reacting a compound of formula IV

IV with an oxidation reagent. Preferably, the oxidation reagent is pyridinium chlorochromate or pyridinium dichromate.

The compound of formula IV is formed by reacting an optically active compound of formula III

III with paraformaldehyde in an organic solvent in the presence of an alkali metal compound under formaldehydation. Preferably, the alkali metal compound is lithium compound, lithium metal oxide phosphate, or lithium metal oxide. More preferably, the alkali metal compound is lithium hexamethyldisilazide. Preferably, the organic solvent is acetonitrile, ethyl acetate, tetrahydrofuran, acetone, propyl ether, butyl ether, t-butanol, toluene, benzene, ethyl ether, isopropyl ether, isobutyl ether, dimethylformamide, or 1,4-dioxane, and reaction temperature of the formaldehydation is between −78° C. and −40° C.

The compound of formula III is formed by reacting an organic compound ketal of chiral diol of a compound of formula VII with glycol and p-toluenesulfonic acid to form a compound of formula VI,

VII

VI and further reacting with a reducing reagent. Preferably, the reducing reagent is diisobutylaluminium hydride.

The organic compound ketal of chiral diol of the compound of formula VII is formed by reacting a chiral diol with a racemic compound of formula VII VII and further separating. Preferably, the chiral diol is compound of formula II

II where $W_1$, $W_2$, $W_3$, and $W'_1$, $W'_2$, $W'_3$ is H, $C_{1-6}$ alkyl, $C_{2-6}$ alkenyl, $C_{2-6}$ alkynyl, halogen, or $C_6H_5$; $X_1$ and $X_2$ is O, S, $C_{1-6}$ alkyl, or NH, $Y_1$, $Y'_1$ and $Y_2$, $Y'_2$ is H, OH, $C_{1-6}$ alkyl, or SH and $Y_1 \neq Y'_1$ and $Y_2 \neq Y'_2$, $Z_1$ and $Z_2$ is H, $C_{1-6}$ alkyl, or $C_6H_5$; and m and n is 0, 1, 2 or 3.

The compound of formula VII is formed by reacting a compound of formula VIII

VIII with trimethylsilyl cyanide in an organic solvent in the presence of alkyl aluminum. Preferably, the alkyl aluminum is triethylaluminum or trimethylaluminum, the organic solvent is acetonitrile, ethyl acetate, tetrahydrofuran, acetone, propyl ether, butyl ether, t-butanol, toluene, benzene, ethyl ether, isopropyl ether, isobutyl ether, dimethylformamide, or 1,4-dioxane.

Since cyanidation is high risk, especially for high concentration of hydrogen cyanide gas and long reaction time, all are difficulties to be overcome. Thus, the present invention used trimethylsilyl cyanide to replace hydrogen cyanide. According to previously published literature (Ihara, M., Katsumata, A., Egashira, M., Suzuki, S., Tokunaga, Y., Fukumoto, K., *J. Org. Chem.* 1995, 60, 5560-5566; Suryawanshi, S. N., Fuchs, P. L., *J. Org. Chem.* 1986, 51, 902-921; Nagata, W., Yoshioka, M., Hirai, S., *J. Am. Chem. Soc.* 1972, 94, 4635-4643; Utimoto K, Wakabayashi Y, Horiie T, Inoue M, Shishiyama Y, Obayashi M, Nozaki H., *Tetrahedron* 1983, 39, 967-973), the asymmetric 1,4-addition reaction of conjugated enone was proceeded with triethylaluminum and trimethylsilyl cyanide to form trans cyanided decalone. The reaction concentration of cyanide ion in solution was increased to reduce reaction time and the formation rate of product was controlled kinetically to increase under irreversible reaction condition. Both strategies further increased the yield of trans cyanided decalone.

Figure 2:
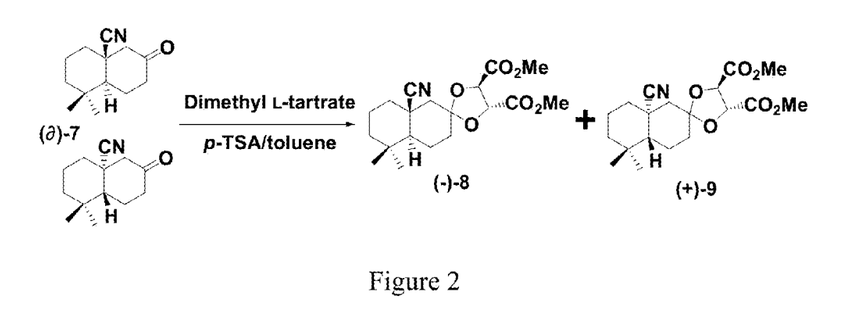
FIG. 2 shows the optical resolution of 1,1-dimethyl-6-oxo-decahydronaphthalene-4a-carbonitrile.

The design strategy of preparing trans-cyanided decalone as starting material was to satisfy the requirement of optical activity. The solution was using natural dimethyl tartarate to react with compound (±)-(7) (Demuth, M., Schaffner, K., U.S. Pat. No. 4,461,687) to form mixture of ketal, which were diastereomers (55:45)—compound (−)-8 and (+)-9 (FIG. 2), and separated by silica gel chromatography to obtain the two diastereomers, respectively.

Thus, using the results of the present invention, intermolecular ketal reaction of the racemic ketone group could be processed with chiral diol (formula 2) in a toluene solvent to achieve optical resolution.

Figure 3:
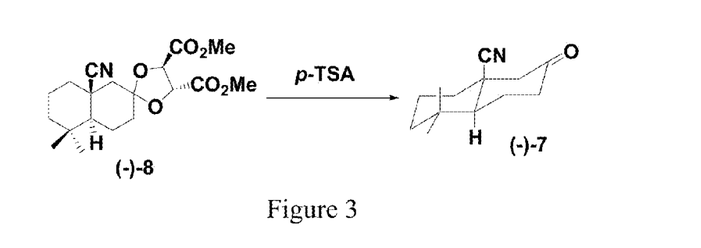
FIG. 3 shows remove of tartrate protection group.
Figure 4:
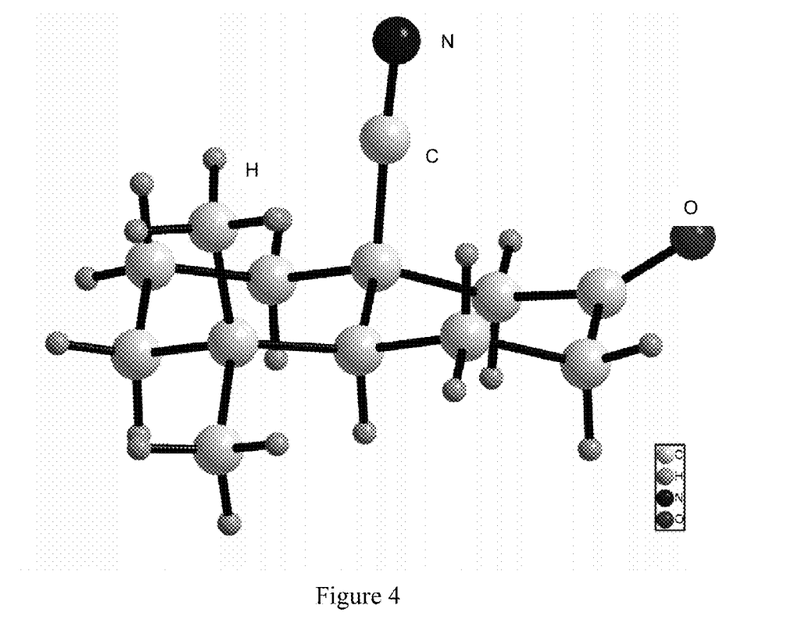
FIG. 4 shows the X-ray diffraction crystal structure of trans-1,1-dimethyl-6-oxo-decahydronaphthalene-4a-carbonitrile—compound (−)-7.

Since the resulting chiral intermediate—compound (−)-8 must be confirmed to conform to the stereo structure of antrocin, the protecting group is removed from the ketal chiral intermediate to obtain compound (−)-7, as shown in FIG. 3. It can provide material for next reaction and the crystal can be validated by X-ray diffraction. FIG. 4 shows the absolute stereo structure of compound (−)-7 is conform to antrocin.

Figure 5:
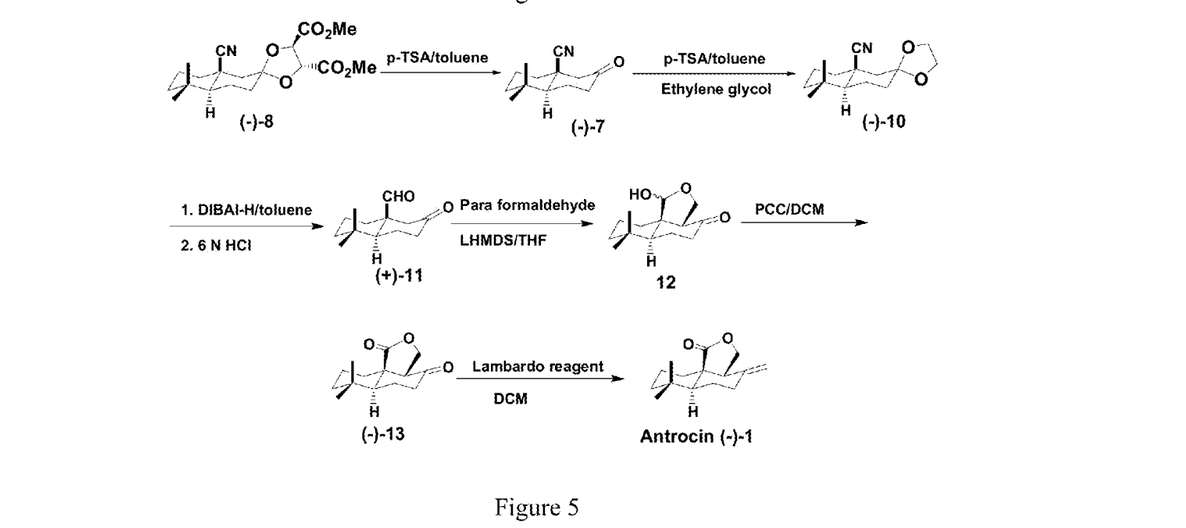
FIG. 5 shows the process of preparing optically active antrocin.

For the demand of target product, the functional group can be added to backbone structure, as shown in FIG. 5. Glycol was substituted for the tartarate protecting group of compound (−)-8 of the present invention in order to reduce cyano group into aldehyde group by diisobutylaluminium hydride (DIBAL) (Zoretic, P. A., Zhang, Y., Fang, H., Ribeiro A. A., Dubay, G., *J. Org. Chem.* 1998, 63, 1162-1167). In further adding acid process, the glycol protecting group was removed to obtain chiral intermediate—compound (+)-11. Next, aldehyde was added to proceed coupling reaction (Kato, M., Hatsumura, Y., Heima, K., Pukamiya, N., Kabuto, C., Yoshikoshi, A., *Tetrahedron*, 43, 711-722). To accept formaldehyde molecule in correct site and obtain stereo structure, the present invention tried a synthesis concept different to traditional, by violent means, using high concentration of aldehyde to increase coupled aldehyde in short time and site specificity to enhance opportunities for coupling. The correct stereo structure formed a stable five-member ring structure with the aldehyde group of compound (+)-11 by means of lactone alcohol. The incorrect stereo structure reversible forced formaldehyde molecules exit the coupling site by the help of additional energy. Although the yield of this incorporation of aldehyde group and formaldehyde to promote the selectivity of stereo site was less than 50% and the product was the mixture of diastereomer—compound 12, the formed antrocin had complete configuration.

The final modifying process converted the lactone alcohol into lactone—compound (−)-13 by PCC oxidation (Luzzio, F. A., Fitch, R. W., Moore, W. J., Kelli, J., Mudd, K. J. *J. Chem. Edu.*, 1999, 76, 974-975). Lombardo reagent was further used for methylenation of ketone group (Lombardo, L., *Tetrahedron Letters*, 1982, 23, 4293-4296; Skepper, C. K., Quach T., Molinski T. F., *J. Am. Chem. Soc.* 2010, 132, 10286-92). After whole synthesis reaction was finished, only using simple wash step, general chromatography operation, and crystallization were needed to purify final product to obtain optically active antrocin. The $^1$H NMR, $^{13}$C NMR, melting point and specific rotation of synthetic antrocin was consistent with natural antrocin.

EXAMPLES

The examples below are non-limiting and are merely representative of various aspects and features of the present invention.

The present invention first used the organic synthesis, by simple and efficient concept: optical resolution assisted with dimethyl tartarate to form optically active molecule and modification of the structure to form required antrocin. Substrates used in the present invention are all commercially available materials. Example 1 followed the steps described in literature (Dailey, O. D. Jr., Fuchs, P. L., *J. Org. Chem.* 1980, 45, 216-236; Armour, A. G., Buchi, G., Eschenmoser, A, Storni, A., *Helv. Chim. Acta.*, 1959, 42, 2233) to prepare the starting material 4,4a,5,6,7,8-hexahydro-5,5-dimethyl-2(3H)-naphthalenone—compound (±)-6.

Example 1

Preparation of compound (±)-6 (4,4a,5,6,7,8-hexahydro-5,5-dimethyl-2(3H)-naphthalenone) from compound 3 (6-methoxy-2-tetralone)

3

Preparation of compound 4 (3,4-dihydro-1,1-dimethyl-6-methoxy-2(1H)-naphthalenone)

Compound 3 (51.1 g; 0.290 mol) was dissolved in 175 mL of benzene and then added dropwise to the suspension of sodium hydride (17.6 g; 0.73 mol) and iodomethane (56.0 mL; 0.90 mol) in 300 mL of benzene at 5-10° C., 40 minutes. The mixture was stirred at 5-10° C. for 30 minutes, and then reacted at room temperature for 15 hours. Ethyl ether (200 mL) was added. The organic phase was washed with water, 10% sodium hydroxide solution, and brine (240 mL), and dried with MgSO$_4$. Solvent was removed and subsequent distillated to obtain methylated crude product; bp: 115-116° C. (0.6-0.65 torr) [literature bp: 108-113° C. (0.5-0.6 torr)]. The crude product was mixed with 85% KOH (51 g), 500 mL of glycol, and 97% hydrazine (68 mL; 2.05 mol), heated to 130° C. over 1 hour, and heated at reflux for 21 hours. After cooling down, the mixture was poured into 600 mL of water, and extracted with n-hexane (5×300 mL). The combined organic layer was washed with brine (225 mL) and dried (MgSO$_4$). The solvent was removed in vacuum to obtain 45.5 g of compound 4 (82.6%) as yellowish liquid.

Next, compound 4 (9.29 g; 48.8 mmol) and 10 mL of ethyl ether and 100 mL of liquid ammonia were placed in 250 mL three-neck flask equipped with dry ice condenser, liquid ammonia inlet, and rubber stopper. Metal lithium (40 mm; 1.69 g, 0.244 mol) was added gradually into the three-neck flask under reflux condition. After 30 minutes, ethanol (14.2 mL; 0.244 mol) was added slowly through dropping funnel over 30 minutes. After 15 minutes, further 10 mL of ethanol was added to mixture, which is still blue. Ammonia was evaporated colorless mixture solution. The residue was extracted and partitioned with 100 mL of water and 50 mL of ethyl ether (3×50 mL). The combined organic layer was washed with 50 mL of brine and dried with magnesium sulfate. The solvent was evaporated to obtain 9.08 g of hydrogenated crude product as soft white solid. The crude product was dissolved in 200 mL of tetrahydrofuran and stirred with 5 mL of concentrated hydrochloric acid for 2 hours. After 20 minutes with no significant change, the reaction mixture was neutralized with 120 mL of saturated sodium bicarbonate solution to separate water layer and organic layer. The water layer was extracted with 120 mL of ethyl ether. The combined organic layer was further washed with brine and dried (MgSO$_4$). The solvent was evaporated under reduced pressure and 100 mL of ethanol was added to heat at reflux for 2 hours to convert compound 5 into compound (±)-6. After solvent concentrated, the residue was purified with silica gel chromatography column, eluted with 5% ethyl acetate-n-hexane. The solvent was removed to obtain 7.32 g of compound (±)-6 (84.7%) as yellow-brown liquid.

IR (KBr, cm$^{-1}$): 3327, 2959, 2871, 1675, 1614, 1453, 1255, 874, 478. HRMS (M$^+$): Calcd. for $C_{12}H_{18}O$: 178.14. Found: 178.

Figure 6:
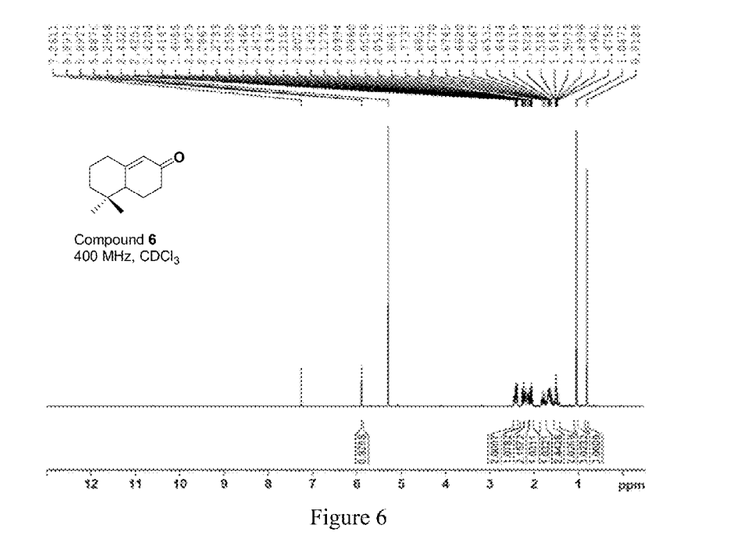
FIG. 6 shows $^1$H NMR (400 MHz, $CDCl_3$) spectrum of compound 6.

$^1$H NMR (400 MHz, CDCl$_3$) δ: 5.29-5.89 (t, 1H, J. 2, 1.8), 0.81 (s, 3H), 1.04 (s, 3H), 2.38-2.43 (m, 2H), 2.05-2.27 (m, 4H), 1.46-1.8 (m, 5H) (FIG. 6).

Figure 7:
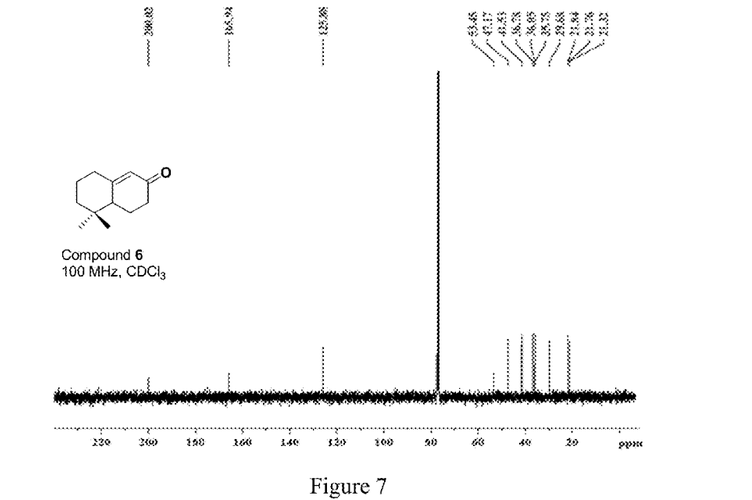
FIG. 7 shows $^{13}$C NMR (100 MHz, $CDCl_3$) spectrum of compound 6.

$^{13}$C NMR (100 MHz, CDCl$_3$) δ: 200.02, 165.94, 125.88, 53.45, 47.17, 41.53, 36.78, 36.05, 35.75, 29.68, 21.84, 21.76, 21.32 (FIG. 7)

Example 2 used new method and reagent to prepare known racemic compound—compound (±)-7.

Example 2

Preparation of 1,1-dimethyl-6-oxo-decahydronaphthalene-4a-carbonitrile—compound (±)-7 through cyanidation by 1,4 addition reaction At 0° C., a solution of 1 M Et$_3$Al in toluene and 5.5 mL of tetrahydrofuran were placed in two-neck flask equipped with rubber stopper and N$_2$ inlet. A solution of TMSCN (0.203 mL; 2.05 mmol) in 10 mL of tetrahydrofuran was added slowly by syringe over 10 minutes. After 20 minutes of stirring, 4,4a,5,6,7,8-hexahydro-5,5-dimethyl-2(3H)-naphthalenone—compound (±)-6 (0.166 g; 0.932 mmol) was slowly added in 10 mL of tetrahydrofuran over 30 minutes. After addition finished, the reaction mixture was returned to room temperature and heated at reflux for 20 hours. Then, the reaction solution was neutralized with saturated NaHCO$_3$ solution and extracted with ethyl acetate (3×20 mL). The organic phase was dried with magnesium sulfate (MgSO$_4$), filtered and the solvent was evaporated under reduced pressure. The resulting residue and 3.5 mL of HIO$_4$ (10% aqueous solution) and 12 mL of tetrahydrofuran were stirred at room temperature for 40 minutes, diluted with water and the reaction mixture was extracted with ethyl acetate (3×20 mL). The combined organic layer was washed with saturated NaHCO$_3$ solution (50 mL), brine (50 mL) and dried (MgSO$_4$), concentrated under reduced pressure to remove the solvent. The residue was purified by silica gel chromatography column, using 10% ethyl acetate-n-hexane as eluting solvent. The solvent was removed to obtain 0.156 g of compound (±)-7 (80%) as white crystal, Mp: 52-53.5° C. IR (KBr, cm$^{-1}$): 3420, 2937, 2869, 2228, 1721, 1455, 1370, 1213,1087, 944, 756, 594, 497. LRMS (M$^+$): Calcd for $C_{13}H_{19}NO$: 205.147 (M$^+$). Found: 205.149.

Figure 8:
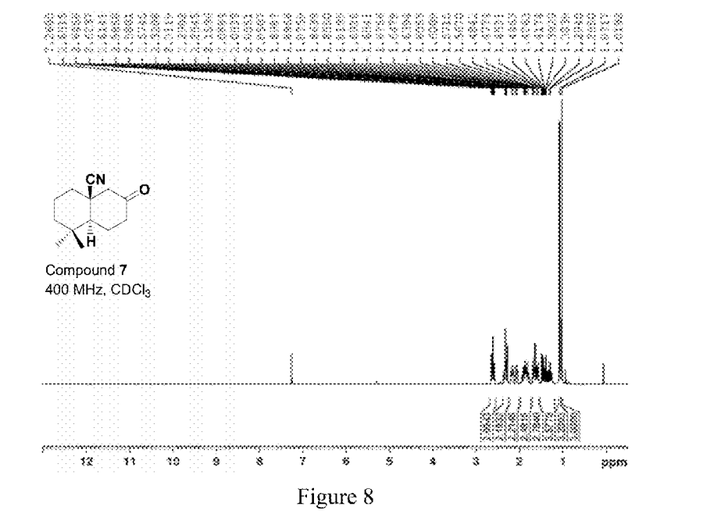
FIG. 8 shows $^1$H NMR (400 MHz, $CDCl_3$) spectrum of compound 7.

$^1$H NMR (400 MHz, CDCl$_3$) δ: 1.019 (s, 3H), 1.071 (s, 3H), 2.57-2.65 (m, 2H), 2.28-2.32 (m, 2H), 2.05-2.15 (m, 2H), 1.8-1.9 (m, 2H), 1.28-1.69 (m, 6H) (FIG. 8) ○

Figure 9:
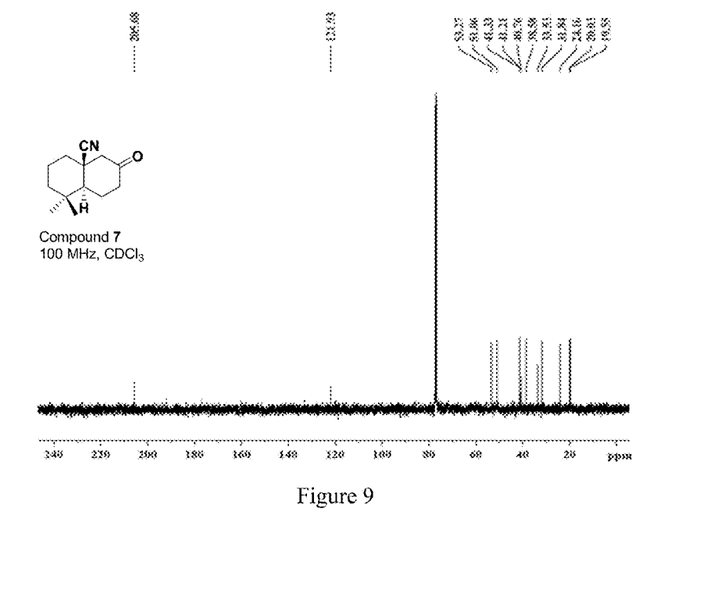
FIG. 9 shows $^{13}$C NMR (100 MHz, $CDCl_3$) spectrum of compound 7.

$^{13}$C NMR (100 MHz, CDCl$_3$) δ: 205.68, 121.93, 53.27, 51.06, 41.33, 41.21, 40.76, 38.58, 33.53, 31.84, 24.16, 20.03, 19.55 (FIG. 9) ○

Next using ketal reaction to perform optical resolution to obtain novel optical isomers.

Example 3

Optical Resolution of trans 1,1-dimethyl-6-oxo-decahydronaphthalene-4a-carbonitrile—compound (±)-7 by dimethyl L-tartarate

Compound (±)-7 (1 g; 4.8 mmol) with dimethyl L-tartarate (4.5 g; 24 mmol) and p-toluenesulfonic acid (p-TSA) were dissolved in 30 mL of toluene solution and equipped with Dean-Stark trap under nitrogen gas and heated at reflux for 24 hours. Then, the reaction solution was cooled down to room temperature and washed with saturated sodium bicarbonate solution (~30 mL). The resulting sodium bicarbonate layer was extracted with ethyl acetate (3×40 mL). The organic layer was combined and dried with magnesium sulfate, filtered and concentrated under reduced pressure to remove solvent to obtain 1.7 g of residue. The residue was separated by silica gel column chromatography (dichloromethane). The solvent was removed to obtain the two diastereomers—compound (−)-8 (626 mg, 35%) and compound (+)-9 (420 mg), respectively. IR (KBr, cm$^{-1}$): 2951, 2867, 2232.93, 1761, 1745, 1629, 1438, 1368,1280, 1217, 1209, 1133,1103, 1057, 1011, 987, 917,812, 748. HRMS(M+H): calcd for $C_{13}H_{19}NO$ (M+H): 266.1838. found: 266.1906. [α]$^{24.5}_D$=−42.7 (c=1; CHCl$_3$).

Figure 10:
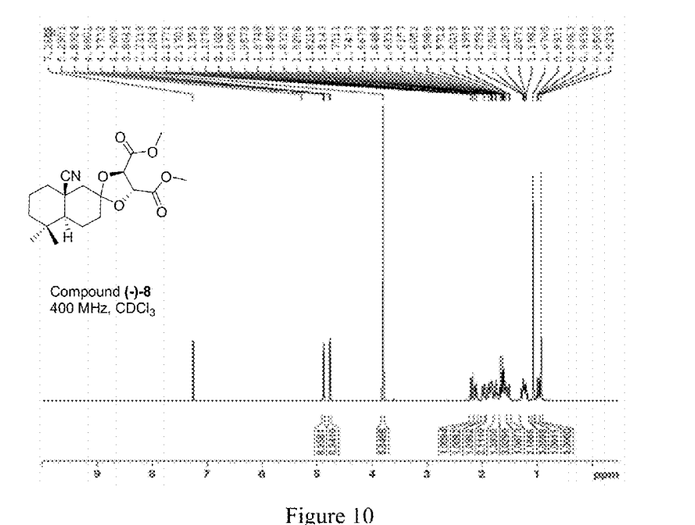
FIG. 10 shows $^1$H NMR (400 MHz, $CDCl_3$) spectrum of compound 8.

(−) 8: $^1$H NMR (400 MHz, CDCl$_3$) δ: 0.924 (s, 3H), 1.07 (s, 3H), 0.95-0.0.99 (dd, 1H, j=2.8, 2.72), 1.19-1.25 (m, 2H), 1.49-1.66 (m, 3H), 1.74-1.87 (m, 3H), 1.95-1.99 (m, 1H), 2.09-2.13 (1H, dd, j=16, 3) 2.17-2.21 (1H, dd, j=16.72 Hz, 2.8 Hz) 4.76 (1H, d, j=4.96 Hz), 4.88-4.89 (1H, d, j=4.92) (FIG. 10).

Figure 11:
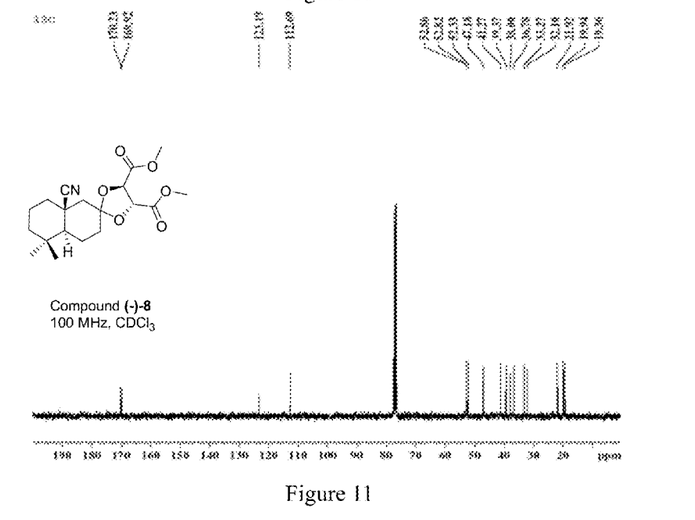
FIG. 11 shows $^{13}$C NMR (100 MHz, $CDCl_3$) spectrum of compound 8.

$^{13}$C NMR (100 MHz, CDCl3) δ: 170.23, 169.92, 123.19, 112.69, 52.86, 52.82, 52.33, 47.18, 41.27, 39.37, 38.00, 36.78, 33.27, 32.10, 21.92, 19.94, 19.36 (FIG. 11).

Example 4

Preparation of trans 1,1-dimethyl-6-(1,3-dioxolane)-decahydronaphthalene-4a-carbonitrile—compound (−)-10

Compound (−)-8 (2.1 g; 5.36 mmol) with glycol (3.6 mL; 53 mmol) and p-TSA were dissolved in 30 mL of toluene solution, and equipped with Dean-Stark trap under nitrogen gas and heated at reflux for 4 hours. Then, the reaction solution was cooled down to room temperature and washed with saturated sodium bicarbonate solution (~30 mL). The resulting sodium bicarbonate layer was extracted with ethyl acetate (3×40 mL). The organic layer was combined and dried with magnesium sulfate, filtered and concentrated under reduced pressure to remove solvent, and purified by silica gel chro- matography column with 10% ethyl acetate-n-hexane as eluting reagent to obtain the purified compound (−)-10 (1.25 g, yield 89%) as white solid, $[\alpha]^{25.8}{}_D=-44.9$ (c=1; CHCl$_3$) ○ IR (KBr, cm$^{-1}$): 3446, 2948, 2934, 2231, 1449, 1366, 1267, 1184, 1119, 1085, 949, 814, 763. HRMS (M$^+$): Calcd for C$_{15}$H$_{23}$NO$_2$: 249.1729 (M$^+$). Found: 249.1733.

Figure 12:
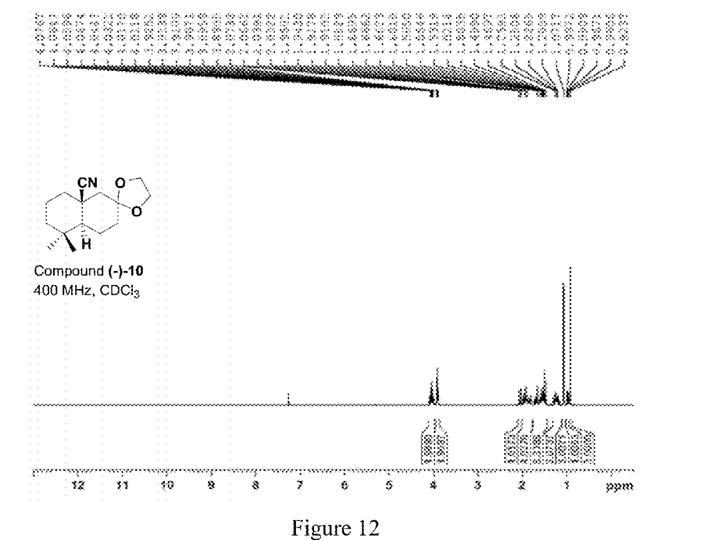
FIG. 12 shows $^1$H NMR (400 MHz, $CDCl_3$) spectrum of compound 10.

$^1$H NMR (400 MHz, CDCl$_3$) δ: 0.923 (s, 3H), 1.07 (s, 3H), 3.89-3.92 (m, 2H), 4.01-4.07 (m, 2H), 2.03-2.073 (dd, 1H, J=2.76, 16.4 Hz), 1.8-1.98 (m, 4H), 1.46-1.70 (m, 5H), 1.19-1.29 (m, 2H), 0.96-0.99 (dd, 1H, J=2.6, 14.64 Hz) (FIG. 12).

Figure 13:
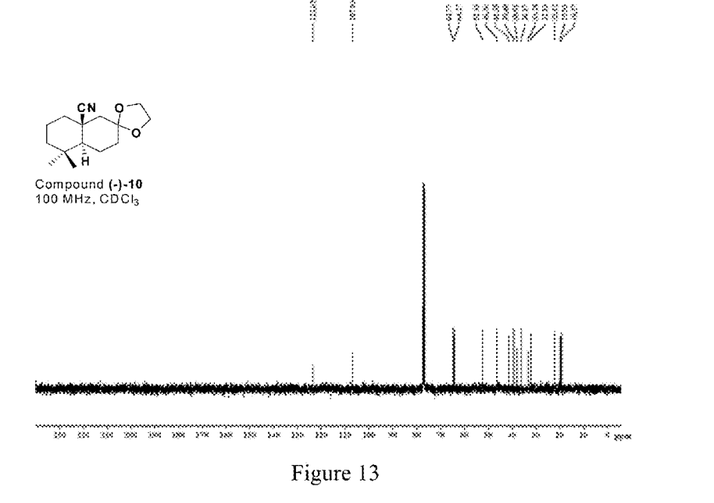
FIG. 13 shows $^{13}$C NMR (100 MHz, $CDCl_3$) spectrum of compound 10.

$^{13}$C NMR (100 MHz, CDCl$_3$) δ: 123.62, 107.03, 64.77, 64.27, 52.43, 46.36, 41.35, 39.40, 38.01, 36.17, 33.28, 32.13, 22.12, 19.93, 19.37 (FIG. 13).

Example 5

Preparation of trans 1,1-dimethyl-6-oxo-decahydronaphthalene-4a-carbaldehyde—compound (+)-11

Compound (−)-10 (443 mg; 1.77 mmol) was dissolved in 4.8 mL of toluene and placed in two-neck flask equipped with rubber stopper and N$_2$ inlet. Diisobutylaluminium hydride (DIBAL, 1M solution in hexane, 2.2 mL; 2.117 mmol) was added slowly by syringe over 10 minutes. After addition, the reaction mixture was stirred for 2 hours. Then, 1 N HCl (20 mL) was added to the reaction mixture at 0° C., diluted with ethyl acetate (10 mL), and further stirred at room temperature for 4 hours. The reaction mixture was extracted with ethyl acetate (10×30 mL). The combined organic extract was washed with saturated solution of NaHCO$_3$, dried with magnesium sulfate, filtered and concentrated under reduced pressure to remove solvent, in high vacuum condition, to obtain semi-solid product—compound (+)-11(370 mg; yield 100%). $[\alpha]^{22.7}{}_D=+5.9$ (c=1; CHCl$_3$) ○ IR (KBr, cm$^{-1}$): 2962, 2877, 1708, 1459, 1376, 1311, 1260, 1223, 1069, 947, 867, 530.

Figure 14:
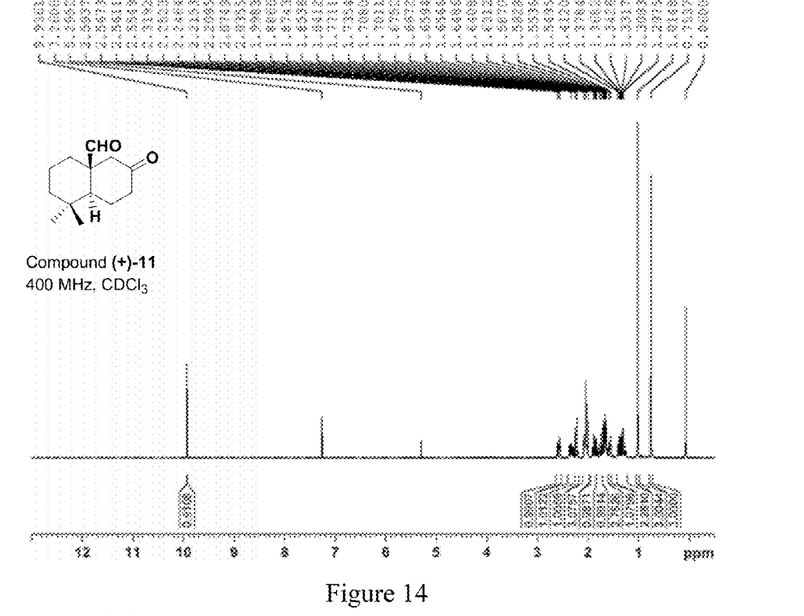
FIG. 14 shows $^1$H NMR (400 MHz, $CDCl_3$) spectrum of compound 11.

$^1$H NMR (400 MHz, CDCl$_3$) δ: 9.93 (s, 1H), 2.55-2.60 (m, 1H), 2.31-2.33 (m, 1H), 2.074-2.25 (dd, 1H, J=2.32, 17.12 Hz), 1.88-2.07 (m, 3H), 1.54-1.88 (m, 5H), 1.29-1.41 (m, 2H), 1.01 (s, 3H), 0.75 (s, 3H) (FIG. 14).

Figure 15:
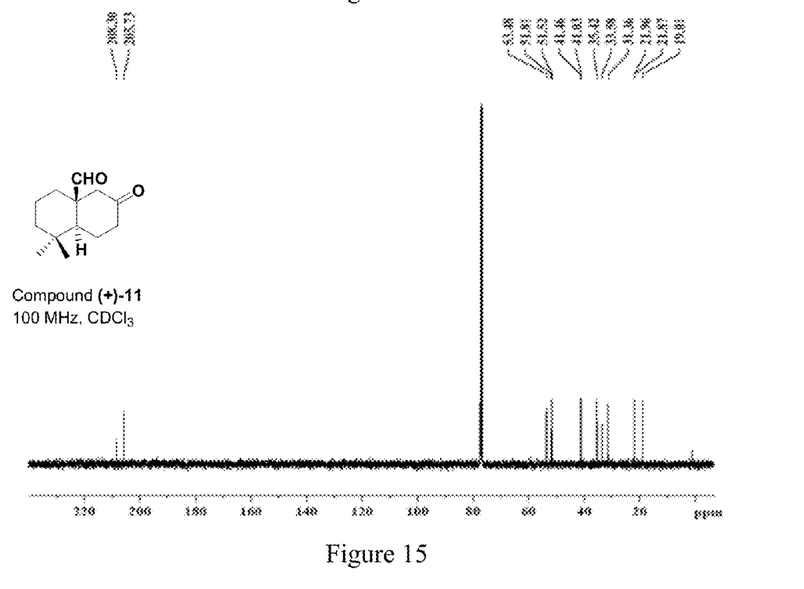
FIG. 15 shows $^{13}$C NMR (100 MHz, $CDCl_3$) spectrum of compound 11.

$^{13}$C NMR (100 MHz, CDCl$_3$) δ: 208.30, 205.73, 53.48, 51.81, 51.52, 41.46, 41.03, 35.42, 33.58, 31.36, 21.96, 21.87, 19.01 (FIG. 15).

Example 6

Preparation of Lactone Alcohol Ketone (1-hydroxy-7,7-dimethyl-4-oxo-decahydro-naphtho[1-c]furan)—Compound 12

Preparation of aldehyde tetrahydrofuran solution: paraformaldehyde (7 g) was placed in 100 mL single-neck round bottom flask in vacuo at 80° C. for 1 hour to dehydrate completely. Then the round bottom flask equipped with rubber stopper and N$_2$ gas was heated to 140-160° C. to form formaldehyde gas monomer, and N$_2$ gas passed through pipe to another single-neck round bottom flask including 40 mL of tetrahydrofuran, stirred at −78° C. for 40 minutes. The resulting tetrahydrofuran solution was used immediately.

Lithium hexamethyldisilazide (LHMDS) was dissolved in 4 mL of tetrahydrofuran, a tetrahydrofuran solution containing compound (+)-11 (0.330 g; 1.584 mmol) was added at −78° C. under stirring, and stirred for 5 hours. The formaldehyde tetrahydrofuran solution (40 mL) was added to the above reaction mixture through the pipe connecting the two round bottom flask at −78° C. After addition, the reaction mixture was stirred at the same temperature for 15 minutes, an aqueous solution of ammonium chloride was added dropwise, and extracted with ethyl ether (3×30 mL). The organic layer extract was combined, washed with water and brine, dried with magnesium sulfate, filtered and concentrated under reduced pressure to remove solvent, in high vacuum condition, to obtain white semi-solid product. Using silica gel chromatography column to separate (ethyl acetate/dichloromethane=10:90) to obtain white solid of compound 12 (180 mg, yield 47.7%). IR (KBr, cm$^{-1}$): 3401, 2950, 2925, 1711, 1457, 1419, 1264, 1096, 1024, 900, 861, 761, 740, 614. HRMS (M$^+$): Calcd for C$_{14}$H$_{22}$O$_3$: 238.1569 (M$^+$). Found: 238.1575.

Figure 16:
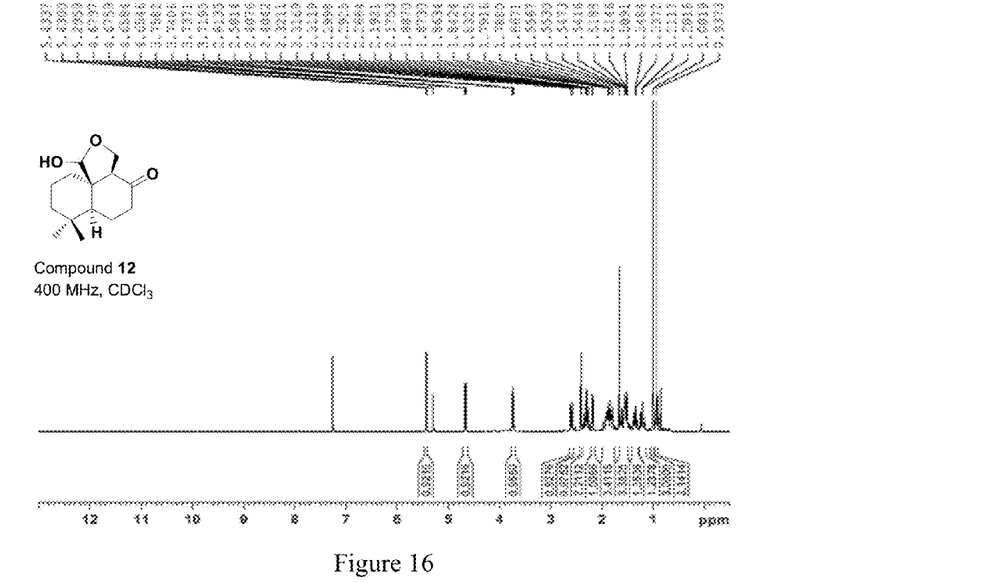
FIG. 16 shows $^1$H NMR (400 MHz, $CDCl_3$) spectrum of compound 12.

$^1$H NMR (400 MHz, CDCl$_3$) δ: 5.4 (s, 1H), 4.65-4.67 (dd, 1H, J=1.52, 10.04 Hz), 3.71-3.75 (t, 1H, J=7.04 Hz), 3.20 (s, 1H), 2.58-2.61 (m, 1H), 2.40 (d, 1H), 2.26-2.32 (m, 2H), 2.17-2.19 (d, 1H, J=6.72 Hz), 1.78-1.92 (m, 3H), 1.50-1.56 (m, 3H), 1.20-1.34 (m, 2H), 1.00 (s, 3H), 0.93 (s, 3H) (FIG. 16).

Figure 17:
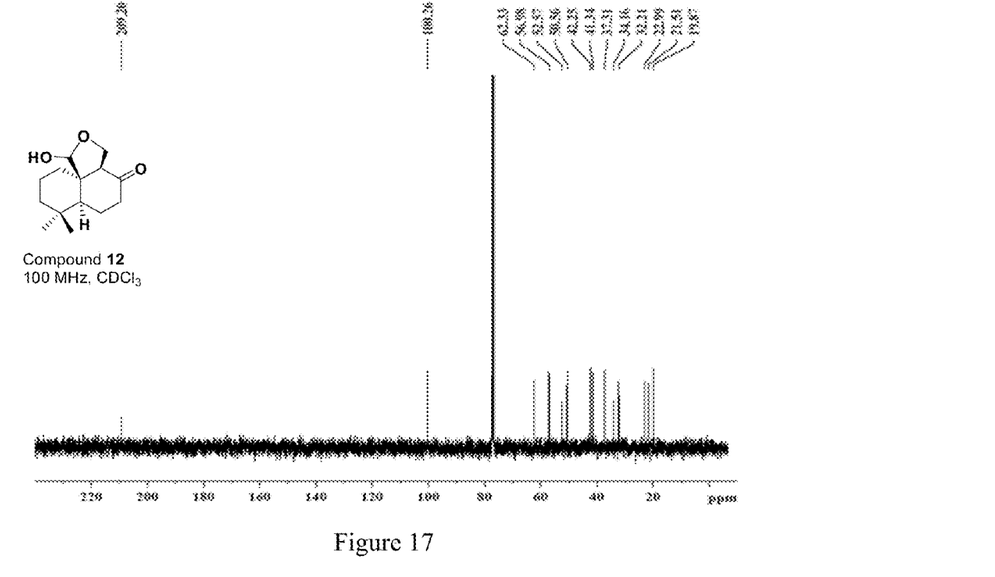
FIG. 17 shows $^{13}$C NMR (100 MHz, $CDCl_3$) spectrum of compound 12.

$^{13}$C NMR (100 MHz, CDCl$_3$) δ: 209.20, 100.26, 62.33, 56.98, 52.57, 50.56, 42.25, 41.34, 37.31, 34.16, 32.21, 22.99, 21.51, 19.87 (FIG. 17).

Example 7

Preparation of Lactone Ketone (7,7-dimethyl-4-oxo-octahydro-naphtho[1-c]furan-1(3H)-one)—Compound (−)-13

Compound 12 (160 mg; 0.67 mmol) was dissolved in dichloromethane (20 mL), pyridinium chlorochromate (PCC, 290.8 mg; 1.35 mmol) was added under stirring at room temperature, further stirred for 6 hours, then diluted with 60 mL of ethyl ether and filtered through Celite. After the filtrate evaporated, white solid was obtained. Using silica gel chromatography column eluted with chloromethane to obtain white solid of compound (−)-13 (137 mg, 86%). IR (KBr, cm$^{-1}$): 3435, 2950, 2918, 2852, 1762, 1718, 1465, 1368, 1262, 1120, 1019, 763, 750, 704, 616. HRMS (M+): Calcd for $C_{14}H_2O_3$: 234.1412. Found: 236.1415. $[\alpha]^{22.7}_D$=(−)−63.4 (c=1; CHCl$_3$).

Figure 18:
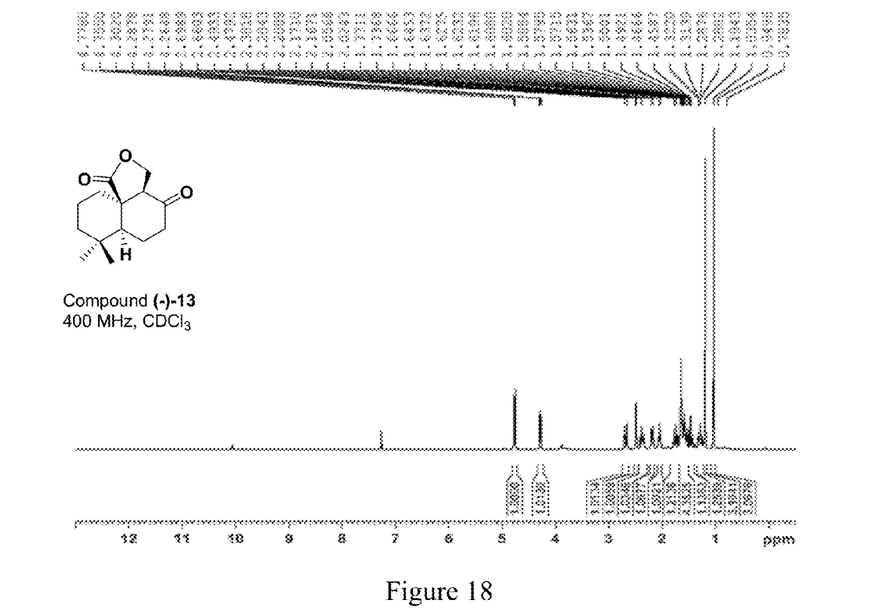
FIG. 18 shows $^1$H NMR (400 MHz, $CDCl_3$) spectrum of compound 13.

$^1$H NMR (400 MHz, CDCl$_3$) δ: 4.77-4.75 (d, 1H, J=9.2 Hz), 4.26-4.30 (m, 1H), 2.66-2.69 (dd, 1H, J=15.4 Hz), 2.47-2.49 (d, 1H, J=5.64 Hz), 2.38 (m, 1H), 2.16-2.20 (dd, 1H, J=1.56, 14.88 Hz), 2.02-2.05 (m, 1H), 1.43-1.77 (m, 5H), 1.28-1.32 (td, 1H, J=2.96, 16.72 Hz), 1.19 (s, 3H), 1.035 (s, 3H) (FIG. 18).

Figure 19:
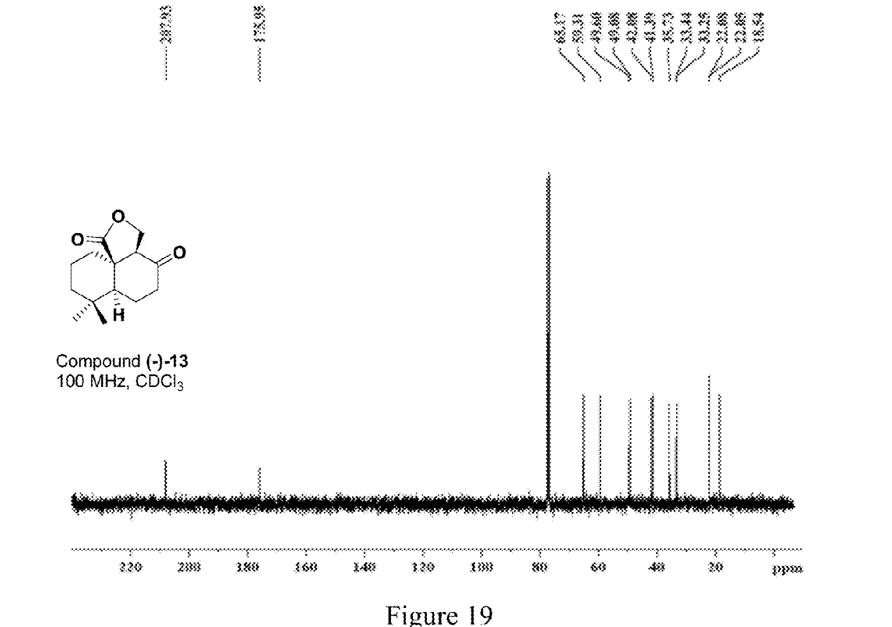
FIG. 19 shows $^{13}$C NMR (100 MHz, $CDCl_3$) spectrum of compound 13.

$^{13}$C NMR (100 MHz, CDCl$_3$) δ: 207.93, 175.95, 65.17, 59.31, 49.60, 49.08, 42.08, 41.39, 35.73, 33.44, 33.25, 22.08, 22.05, 18.58 (FIG. 19).

Example 8

Preparation of Antrocin—Compound (−)-1

Preparation of Lombardo reagent Zinc powder (571 mg; 8.73 mmol) was placed in 20 mL bottle equipped with rubber stopper, dried shortly with flame under high vacuum. After cooling down, the bottle was filled with N$_2$, anhydrous tetrahydrofuran (7.1 mL), 1,2-dibromoethane (82 mg; 0.44 mmol), and trimethylsilyl chloride (TMSCl, 9.5 mg; 0.087 mmol) were added. After stirring for 10 minutes, dibromomethane (494 mg; 2.84 mmol) was added. After the mixture was cooled down to −40° C., TiCl$_4$ (385 mg; 2.03 mol) was slowly added over 5-10 minutes. The dark thick mixture was warmed to 0° C. over 45 minutes. After 20 hours, 1 mL of anhydrous tetrahydrofuran was added to assist stirring. Stirring at this temperature for two day, Lombardo reagent can be obtained.

Preparation of antrocin: Lombardo reagent (400 μL; 0.161 mmol) was added to a solution of dichloromethane (600 μL) containing lactone compound (−)-13 (10 mg; 0.0423 mmol) at 0° C. After the mixture was warmed to room temperature, the mixture was stirred for 30 minutes, then diluted with ethyl ether (2 mL) and extracted with saturated NaHCO$_3$ (2 mL). The resulting two-phase mixture was stirred vigorously for 5 minutes, and the organic layer and water layer were separated. The water layer was extracted with ethyl ether (2×2 mL). The combined organic layer was washed with brine (2 mL), dried with magnesium sulphate, and concentrated under reduced pressure, separated by silica gel chromatography column (ethyl acetate/n-hexane=10:90) to obtain white crystal solid of compound (−)-1 (9.7 mg, yield 98%).HRMS (FAB$^+$): Calcd for $C_{15}H_{22}O_2$: 234.1620 (M$^+$). Found: 234.1624.

Figure 20:
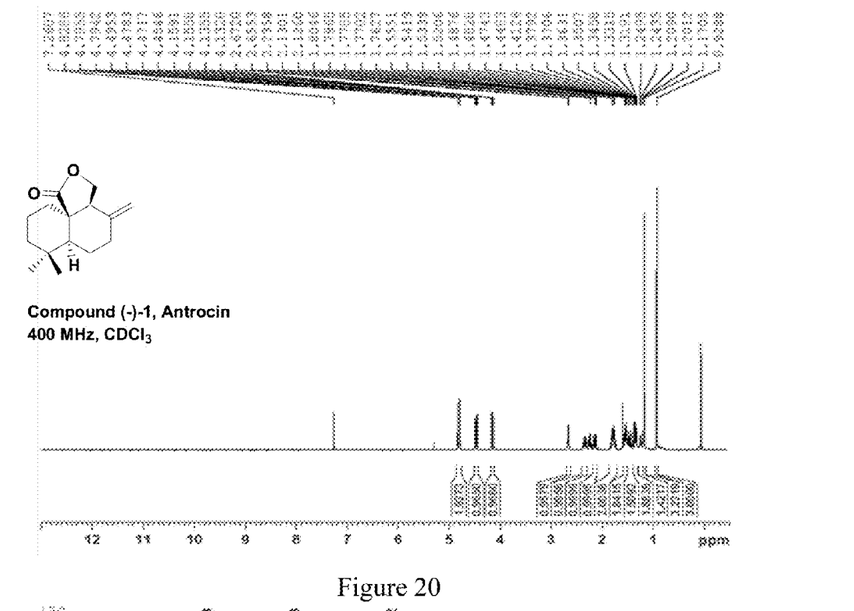
FIG. 20 shows $^1$H NMR (400 MHz, $CDCl_3$) spectrum of compound (−)-1, antrocin.

$^1$H NMR (400 MHz, CDCl$_3$) δ: 0.92 (s, 3H), 1.17 (s, 3H), 1.20-1.24 (dd, 1H, j=3.12, 2.4, 5.88, 19.32 Hz), 1.31-1.37 (m, 2H), 1.40-1.56 (m, 3H), 1.76-1.81 (m, 2H), 2.12-2.15 (dm, 1H, J=1.64, 15.08 Hz), 2.16-2.13 (m, 1H), 2.32 (m, 1H), 2.65-2.67 (d, 1H, J=6.68 Hz), 4.13-4.15 (dd, 1H, J=1.4, 1.32, 10.84, 8.12 Hz), 4.45-4.49 (q, 1H, J=6.84, 2.64, 6.8), 4.794-4.795 (d, 1H, J=0.52 Hz), 4.82 (s, 1H) (FIG. 20).

Figure 21:
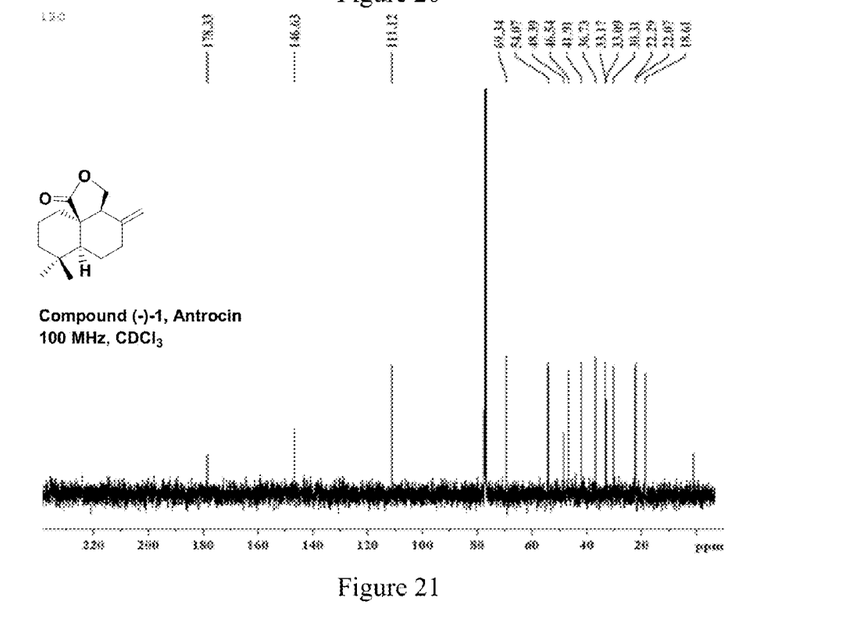
FIG. 21 shows $^{13}$C NMR (100 MHz, $CDCl_3$) spectrum of compound (−)-1, antrocin.

$^{13}$C NMR (100 MHz, CDCl$_3$) δ: 178.33, 146.63, 111.12, 69.34, 54.07, 48.39, 46.54, 41.91, 36.73, 33.17, 33.03, 30.31, 22.29, 22.07, 18.68 (FIG. 21).

IR (KBr, cm$^{-1}$): 3073, 2950, 2856, 1766, 1724, 1662, 1456, 1444, 1376, 1261, 1100, 1120, 1063, 1019, 986, 897, 797, 747, 498 o

What is claimed is:

1. A method for preparing an optically active antrocin of formula I, comprising:

I reacting a compound of formula V with a methylenation reagent to obtain the compound of formula I.

2. The method of claim 1, wherein the methylenation reagent is Lombardo reagent, dimethylzinc, or a mixture of zinc powder, 1,2-dibromoethane, dibromomethane, and trimethylsilyl chloride.

3. The method of claim 1, wherein the compound of formula V is formed by reacting a compound of formula IV with an oxidation reagent.

4. The method of claim 3, wherein the oxidation reagent is pyridinium chlorochromate or pyridinium dichromate.

5. The method of claim 3, wherein the compound of formula IV is formed by reacting an optically active compound of formula III with paraformaldehyde in an organic solvent in the presence of an alkali metal compound under formaldehydation.

6. The method of claim 5, wherein the alkali metal compound is lithium compound, lithium metal oxide phosphate, or lithium metal oxide.

7. The method of claim 5, wherein the organic solvent is acetonitrile, ethyl acetate, tetrahydrofuran, acetone, propyl ether, butyl ether, t-butanol, toluene, benzene, ethyl ether, isopropyl ether, isobutyl ether, dimethylformamide, or 1,4-dioxane.

8. The method of claim 5, wherein reaction temperature of the formaldehydation is between $-78°$ C. and $-40°$ C.

9. The method of claim 5, wherein the compound of formula III is formed by reacting a compound $(-)$-8 with glycol and p-toluenesulfonic acid to form a compound of formula VI, and further reacting with a reducing reagent.

10. The method of claim 9, wherein the reducing reagent is diisobutylaluminium hydride.

11. The method of claim 9, wherein the compound $(-)$-8 is formed by reacting a dimethyl L-tartarate with a racemic compound of formula VII and further separating.

* * * * *